United States Patent
Yuan et al.

(10) Patent No.: US 11,286,318 B2
(45) Date of Patent: Mar. 29, 2022

(54) TEMPERATURE SENSITIVE CELL CULTURE SURFACE AND PREPARATION METHOD THEREOF

(71) Applicant: Guangzhou Jet Bio-Filtration Co., Ltd., Guangzhou (CN)

(72) Inventors: Jianhua Yuan, Guangzhou (CN); Yong Chen, Guangzhou (CN); Huilun Li, Guangzhou (CN); Xiangyuan Fang, Guangzhou (CN)

(73) Assignee: GUANGZHOU JET BIO-FILTRATION CO., LTD., Guangzhou (CN)

( * ) Notice: Subject to any disclaimer, the term of this patent is extended or adjusted under 35 U.S.C. 154(b) by 507 days.

(21) Appl. No.: 15/775,695

(22) PCT Filed: Jan. 29, 2016

(86) PCT No.: PCT/CN2016/072754
§ 371 (c)(1),
(2) Date: Jul. 26, 2018

(87) PCT Pub. No.: WO2017/080116
PCT Pub. Date: May 18, 2017

(65) Prior Publication Data
US 2018/0327526 A1    Nov. 15, 2018

(30) Foreign Application Priority Data
Nov. 13, 2015 (CN) .......................... 201510780506.3

(51) Int. Cl.
C08F 112/08 (2006.01)
C12M 3/04 (2006.01)
(Continued)

(52) U.S. Cl.
CPC .......... C08F 112/08 (2013.01); C08F 257/02 (2013.01); C08F 293/00 (2013.01);
(Continued)

(58) Field of Classification Search
CPC ............ C08F 112/08; C12M 3/00; A61F 2/06
See application file for complete search history.

(56) References Cited

U.S. PATENT DOCUMENTS 8,585,753 B2 * 11/2013 Scanlon .................. A61L 31/10
623/1.42

FOREIGN PATENT DOCUMENTS

| CN | 101914484 A | 12/2010 |
| CN | 102533632 A | 7/2012 |

(Continued)

OTHER PUBLICATIONS

Machine translation of CN 103436444 (Year: 2013).*
(Continued)

*Primary Examiner* — Dah-Wei D. Yuan
*Assistant Examiner* — Andrew J Bowman
(74) *Attorney, Agent, or Firm* — Kagan Binder, PLLC

(57) ABSTRACT

The invention provides a temperature sensitive cell culture surface and preparation method thereof. The preparation method comprises the following steps: (1) preparing a temperature sensitive primary liquid by adding a temperature sensitive compound and a free radical into a solvent, mixing and dissolving the same, and obtaining the temperature sensitive primary liquid; and (2) distributing the temperature sensitive primary liquid on a cell culture surface, and leaving the cell culture surface at 50-150° C. to react for 5-120 mins.

9 Claims, 1 Drawing Sheet

(51) Int. Cl.
*C08F 257/02* (2006.01)
*C08J 7/12* (2006.01)
*C08F 293/00* (2006.01)
*C08L 25/06* (2006.01)
*C12M 1/26* (2006.01)

(52) U.S. Cl.
CPC ............... *C08J 7/12* (2013.01); *C08L 25/06* (2013.01); *C12M 3/04* (2013.01); *C12M 33/00* (2013.01); *C08J 2325/06* (2013.01)

(56) References Cited

FOREIGN PATENT DOCUMENTS

| CN | 103436444 A | * | 12/2013 | ............ C08F 112/08 |
|---|---|---|---|---|
| CN | 103436444 A | | 12/2013 | |
| CN | 104788707 A | | 7/2015 | |
| CN | 105219644 A | | 1/2016 | |
| EP | 2348099 A1 | | 7/2011 | |
| EP | 2471899 A1 | | 7/2012 | |
| EP | 2781594 A1 | | 9/2014 | |
| EP | 2471899 | * | 7/2020 | ............ C12M 3/00 |
| WO | 2017080117 A1 | | 5/2017 | |

OTHER PUBLICATIONS

E1, Atomization, 2011, Thermopedia, pp. 1-12 (Year: 2011).*
Unpublished United States Utility U.S. Appl. No. 15/775,678, filed May 11, 2018.
First Search Report of Chinese Counterpart CN2015107805063 (1 page).
Liu Dan. et al., "Intelligent Cell Detachment Materials Based on Poly (N-Isopropylacrylamide)" Progress in Chemistry, vol. 23, No. 11, Nov. 23, 2011, (pp. 2353-2359). English Abstract and International Search Report for International Apln. No. PCT/CN2016/072754.
International Search Report and English translation thereof for International Application No. PCT/CN2016/072754, dated Aug. 19, 2016 (6 pages).

* cited by examiner

TEMPERATURE SENSITIVE CELL CULTURE SURFACE AND PREPARATION METHOD THEREOF

TECHNICAL FIELD

The present disclosure relates to the technical field of cell culture, particularly to a temperature-sensitive cell culture surface and a preparation method thereof.

BACKGROUND

In recent years, technologies in tissue regeneration engineering, biomedical engineering, and cell therapy industry have developed rapidly. It has become an important direction to produce a large quantity of cells, extracellular secretions, and cell therapy products by large-scale in vitro culture of animal or human cells in current clinical application of cells. For example, skin cell culture and new skin acquisition in tissue trauma or burn treatment, tumor cell therapy, cell cosmetology, and cell slimming all require in vitro culture of target cells.

Cells are mainly divided into suspension cells and adherent cells according to their in vitro culture characteristics. The suspension cells are suspended in the culture medium in the culture device, while the adherent cells needs to adhere to a surface of the culture device to grow. After completion of culture, the adherent cells are detached from the adherent surface primarily by trypsin digestion to complete the harvest. However, such a digestion mode will destroy the membrane proteins on the cell surface, and further the cell integrity. Cells losing integrity is greatly limited in their application, especially in the field of clinical application of cells.

Currently, commercialized temperature-sensitive cell culture surfaces are available in the market and achieved mainly by grafting a temperature-sensitive material on a surface of a culture device. Such a surface allows the cells to automatically detach by changing the temperature after completion of cell culture, reducing the damage to the cells.

Among existing methods for preparing a temperature-sensitive cell culture surface, some of them are provided by the ways of physically coating a temperature-sensitive compound directly on a surface of a cell culture device, the temperature-sensitive response function achieved in such way is unstable, the temperature-sensitive compound will fall off during culture, and therefore the effect of automatic cell detachment cannot be guaranteed; a majority of other methods initiate the grafting of the temperature-sensitive compound on the cell culture surface by high-energy electron beams, and a minority of other methods initiate grafting by ultraviolet irradiation, by plasma, or by atom transfer radicals. Among the ways for realizing the grafting of temperature-sensitive compound on the culture surface, some require expensive production equipment (e.g., high-energy electron beams, plasma), some require complicated process and costly raw materials and are not beneficial to industrialization (e.g., atom transfer radical initiation, ultraviolet irradiation initiation), and some lead to a low grafting efficiency and serious environmental pollution (e.g., plasma).

SUMMARY

Based on this, it is necessary to provide a method for preparing an environment-friendly temperature-sensitive cell culture surface with a high grafting rate and a low production cost.

A method for preparing a temperature-sensitive cell culture surface comprises the following steps:

(1) preparing a temperature-sensitive stock solution: the temperature-sensitive compound and the radical initiator are added to a solvent, stirred and dissolved to obtain a temperature-sensitive stock solution having a mass ratio of the temperature-sensitive compound and the solvent of (2 to 50):100 and a molar ratio of the radical initiator and the temperature-sensitive compound of (0.5 to 50):100;

(2) disposing the cell culture surface under a condition of 50 to 150° C. to react for 5 to 120 min after distributing the temperature-sensitive stock solution on the cell culture surface, so as to obtain a temperature-sensitive cell culture surface.

The reaction of step (2) can be carried out under nitrogen protection as required.

In one embodiment, the distributing method in step (2) is dipping, atomizing, spraying or smearing.

In one embodiment, the dipping method is to dip the cell culture surface into the temperature-sensitive stock solution for 0.1 to 60 min and then take it out;

the atomizing method is to atomize the temperature-sensitive stock solution into particles having a particle size of 2 to 1000 microns, then expose the cell culture surface to the atomized atmosphere for 5 to 100 min, and then take it out;

the spraying method is to spray the temperature-sensitive stock solution on the cell culture surface by high-pressure spraying or air spraying.

In one embodiment, the temperature-sensitive compound is one or more of N-isopropyl acrylamide, N-isopropyl methacrylamide, N-isopropyl acrylamide oligomers, N-isopropyl methacrylamide oligomers, and materials for preparing the cell culture surface is polyolefin or polycarboxylate.

In one embodiment, polyolefin is polystyrene, polypropylene, or polyethylene, and polycarboxylate is polycarbonate, polyfatty acid ester, polyaromatic acid ester, or polyacrylate.

In one embodiment, the radical initiator is one or more of a peroxide initiator (such as, benzoyl peroxide, cumene peroxide, potassium persulfate, tert-butyl peroxide, and the like) and an azo initiator (such as, azodiisobutyronitrile, azobisisoheptonitrile, azobis isobutylamidine hydrochloride (AIBA), azobis isobutyl imidazoline hydrochloride (AIBI), and the like).

In one embodiment, the solvent is one or more of alcohols (such as, methanol, ethanol, propanol, and isopropanol), esters (such as, formates such as methyl formate, ethyl formate, propyl formate, and butyl formate; and acetates such as methyl acetate, ethyl acetate, propyl acetate, and butyl acetate), ketones (acetone, butanone, and the like), chlorinated hydrocarbons (chloroform, dichloromethane, chloroethane, and the like).

The disclosure further provides a temperature-sensitive cell culture surface prepared by the method for preparing the temperature-sensitive cell culture surface.

The present disclosure further provides a cell culture device having the temperature-sensitive cell culture surface.

In one embodiment, the cell culture device is a cell culture plate, a cell culture flask, a cell culture dish, a cell culture device provided with a three-dimensional network structure consisting of multilayer fibers, or a cell culture device provided with particle microcarriers.

Compared with the prior art, the present disclosure has the following beneficial effects:

The method for preparing the temperature-sensitive cell culture surface of the present disclosure allows to reasonably figure out the concentrations of the temperature-sensitive compound and the radical initiator in the temperature-sensitive stock solution, distribute the temperature-sensitive stock solution on the cell culture surface, directly initiate a graft polymerization of temperature-sensitive compound on cell culture surface by using common chemical radical initiator, so as to obtain a cell culture surface having a temperature-sensitive response function; compared with high-energy electron beams and plasma grafting, the method enables a low amount of temperature-sensitive raw material and high grafting efficiency without purchasing large expensive equipments; and compared with the ultraviolet light irradiation and the atom transfer radical initiation, the initiator has a wide raw material sources and a low cost, and its process principle facilitates a large-scale preparation. The temperature-sensitive cell culture surface prepared according to the present disclosure enables the adherent cells to achieve temperature-sensitive detachment by lowering the temperature after the completion of cell culture, reduces the damage of chemically digesting detachment or detachment by physical method to the cells, and guarantees the integrity of cell membrane proteins. Compared with the prior art, the temperature-sensitive cell culture surface has a greatly reduced production cost, and a high grafting rate and is environmental friendly.

Further, in the study of the preparation method, it is found that the method for distributing the temperature-sensitive stock solution have a relatively critical influence on the final grafting rate. The present disclosure preferably uses dipping, atomizing, and spraying under specific conditions to realize the grafting of the temperature-sensitive stock solution on the cell culture surface, which can effectively increase the grafting rate.

DETAILED DESCRIPTION OF EMBODIMENTS

Figure 1:
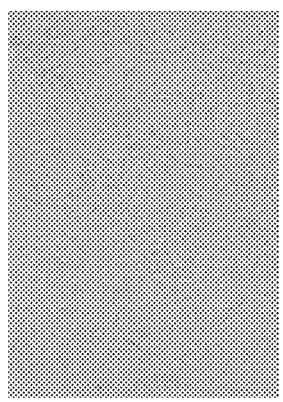
FIG. 1 is a micrograph of T3T cells adhered to a surface of the device by using a temperature-sensitive cell culture surface according to an embodiment of the present disclosure after culturing at 37° C. for 48 hours.

The temperature-sensitive cell culture surface of the present disclosure and a preparation method thereof will be further described in detail with reference to specific examples.

Example 1

0.5 g of N-isopropyl acrylamide monomer was weighed and dissolved along with an azo initiator (the molar ratio of the azo initiator to the monomer was 5:100) in 7.5 g of mixed solvent of isopropanol and ethyl acetate. The mixture solution was atomized into particles having a particle size of 2 to 1000 microns by an atomizer, and then a surface of a cell culture plate to be treated, which was made of polystyrene material, was exposed to an atomized vapor atmosphere for 50 minutes to allow the vapor to condense on the surface to be treated. Finally, the cell culture plate was placed in a nitrogen-filled oven and incubated at 50 to 120° C. for 50 minutes before taken out, so as to obtain a cell culture plate having a temperature-sensitive cell culture surface, with a grafting rate of 2.2 µg/cm².

Example 2

0.7 g of N-isopropyl methacrylamide monomer was weighed and dissolved along with a peroxide initiator (the molar ratio of the peroxide initiator to the monomer was 20:100) in 10 g of mixed solvent of ethanol, propyl formate and dichloromethane. The temperature-sensitive mixture solution was then uniformly sprayed on a surface of a cell culture dish made of polypropylene material by high-pressure spraying. Finally, the cell culture dish was placed in a helium-filled oven and incubated at 90 to 120° C. for 20 minutes before taking out, so as to obtain a cell culture dish having a temperature-sensitive cell culture surface, with a grafting rate of 1.7 µg/cm².

Example 3

0.6 g of N-isopropyl acrylamide monomer was weighed and dissolved along with an azo initiator (the molar ratio of the azo initiator to the monomer was 30:100) in 6 g of mixed solvent of isopropanol, butyl acetate and dichloromethane. The mixture solution was then sprayed on a surface of a cell culture flask made of polystyrene material by air spraying. Then, the cell culture flask was placed in an air-filled oven and incubated at 50 to 120° C. for 30 minutes before taking out, so as to obtain a cell culture flask having a temperature-sensitive cell culture surface, with a grafting rate of 1.5 µg/cm².

Example 4

3.5 g of N-isopropyl acrylamide monomer was weighed and dissolved along with an azo initiator (the molar ratio of the azo initiator to monomer was 40:100) in 7 g of mixed solvent of chloroethane, ethanol and ethyl formate. The mixture solution was then atomized into particles having a particle size of 2 to 1000 microns by high-pressure air atomizing, and then microsphere carriers to be treated, which was made of polyethylene and has a particle size of 40 to 500 microns, were exposed to an atomized vapor atmosphere for 10 minutes to enable the vapor to condense on a surface of the microsphere carriers to be treated. Finally, the microsphere carriers were placed in a nitrogen-filled oven and incubated at 50 to 120° C. for 60 minutes before taking out so as to obtain microsphere carriers having a temperature-sensitive cell culture surface, with a grafting rate of 1.6 µg/cm².

The spherical particle microcarriers can be placed in a conventional cell culture plate, cell culture flask or cell culture dish. After a culture medium was added, fine particles were used as carriers for cell adhesion and growth and suspended in the culture medium by stirring, so that the cell were propagated into a monolayer cell on the surface of the carriers. Since the temperature-sensitive grafting was achieved on the particle microcarriers, they became a temperature-sensitive cell culture device when used in conjunction with a cell culture device, such as a conventional cell culture plate, cell culture flask, cell culture dish, and the like.

Example 5

0.3 g of N-isopropyl acrylamide monomer was weighed and dissolved along with a peroxide initiator (the molar ratio of the peroxide initiator to monomer was 1:100) in 6 g of mixed solvent of ethanol, ethyl acetate and acetone. A multi-layered three-dimensional network porous fibrous scaffold to be treated, which was made of polycarbonate, was dipped in the temperature-sensitive mixed solution for 0.1 to 60 minutes, followed by taking out and air drying. Finally, the scaffold was placed in a nitrogen-filled oven and incubated at 80 to 150° C. for 30 minutes before taking out, so as to obtain a multi-layered three-dimensional network porous fibrous scaffold having a temperature-sensitive cell culture surface, with a grafting rate of 1.5 μg/cm².

The multi-layered three-dimensional network porous fibrous scaffold, as a multi-layered network structure, was allowed to place in a conventional cell culture plate, cell culture flask or cell culture dish as a multi-layer temperature-sensitive scaffold, multiply a specific surface area of cell adhesion and growth and harvest more cells in a limited volume without changing the specification of the conventional cell culture plate, cell culture flask or cell culture dish which matches with the scaffold.

Figure 2:
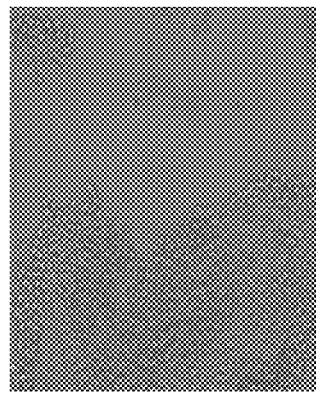
FIG. 2 is a micrograph of automatic detachment of a sheet of cells after disposing the temperature-sensitive cell culture surface at 20° C. for 10 to 40 minutes.

The temperature-sensitive cell culture device prepared in Example 1 was used for T3T cell culture. After the T3T cells were cultured at 37° C. for 48 hours, a micrograph of the cell adhesion was shown in FIG. 1, and after treated at 20° C. for 10 to 40 minutes, a micrograph of automatic detachment of a sheet of cell was shown in FIG. 2.

The technical features of the above-described embodiments may be combined arbitrarily. To make the description brief, all the possible combinations of the technical features in the above embodiments have not been described. However, the combination of these technical features should be considered as falling within the scope described in this specification so long as there is no contradiction.

The above-mentioned embodiments merely represent several embodiments of the present disclosure, and the description thereof is comparatively specific and detailed, but it should not be construed as limiting the scope of the disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims

What is claimed is:

1. A method for preparing a temperature-sensitive cell culture surface comprising the following steps:
   (1) preparing a temperature-sensitive stock solution: a temperature-sensitive compound and a radical initiator are added to a solvent, stirred and dissolved to obtain a temperature-sensitive stock solution having a mass ratio of the temperature-sensitive compound and the solvent of (2 to 50):100 and a molar ratio of the radical initiator and the temperature-sensitive compound of (0.5 to 50):100;
   (2) disposing the cell culture surface under a condition of 50 to 150° C. to react for 5 to 120 min after distributing the temperature-sensitive stock solution on the cell culture surface, so as to obtain a temperature-sensitive cell culture surface,
   wherein distributing the temperature-sensitive stock solution on the cell culture surface in step (2) comprises atomizing the temperature-sensitive stock solution into particles having a particle size of 2 to 1000 microns to form an atomized atmosphere, exposing the cell culture surface to the atomized atmosphere for 5 to 100 min, and then removing the cell culture surface from the atomized atmosphere wherein the temperature-sensitive compound is chosen from N-isopropyl acrylamide, N-isopropyl methacrylamide, N-isopropyl acrylamide oligomers, N-isopropyl methacrylamide oligomers, and combinations thereof.

2. The method according to claim 1, wherein the cell culture surface is made of material comprising polyolefin or polycarboxylate.

3. The method according to claim 2, wherein polyolefin is polystyrene, polypropylene, or polyethylene, and polycarboxylate is polycarbonate, polyfatty acid ester, polyaromatic acid ester, or polyacrylate.

4. The method according to claim 1, wherein the radical initiator is a peroxide initiator and/or an azo initiator.

5. The method according to claim 1, wherein the solvent is one or more of alcohols, esters, ketones and chlorinated hydrocarbons.

6. The method according to claim 2, wherein the radical initiator is a peroxide initiator and/or an azo initiator.

7. The method according to claim 3, wherein the radical initiator is a peroxide initiator and/or an azo initiator.

8. The method according to claim 2, wherein the solvent is one or more of alcohols, esters, ketones and chlorinated hydrocarbons.

9. The method according to claim 3, wherein the solvent is one or more of alcohols, esters, ketones and chlorinated hydrocarbons.

* * * * *